United States Patent
Blake et al.

(10) Patent No.: US 7,337,672 B2
(45) Date of Patent: Mar. 4, 2008

(54) METHOD FOR INSPECTING GRINDING WHEELS

(75) Inventors: Robert A. Blake, Apollo, PA (US); Neville Whittle, Irwin, PA (US); Michelle M. Teichman, Pittsburgh, PA (US)

(73) Assignee: Alcoa Inc., Pittsburgh, PA (US)

( * ) Notice: Subject to any disclaimer, the term of this patent is extended or adjusted under 35 U.S.C. 154(b) by 0 days.

(21) Appl. No.: 11/176,981

(22) Filed: Jul. 8, 2005

(65) Prior Publication Data

US 2006/0063473 A1    Mar. 23, 2006

Related U.S. Application Data

(63) Continuation-in-part of application No. 10/694,649, filed on Oct. 27, 2003, now abandoned.

(51) Int. Cl.
*G01N 9/36* (2006.01)
*B24B 49/00* (2006.01)

(52) U.S. Cl. .................. 73/600; 73/599; 73/602; 451/8; 451/48

(58) Field of Classification Search .................. 73/600, 73/602, 622, 628, 641, 597, 660, 619, 599; 702/180, 137, 199; 451/8, 48
See application file for complete search history.

(56) References Cited

U.S. PATENT DOCUMENTS

| | | | |
|---|---|---|---|
| 3,526,836 A * | 9/1970 | Deger et al. ............... 324/73.1 |
| 4,364,264 A | 12/1982 | Re Fiorentin | |
| 4,603,583 A | 8/1986 | Heumuller | |
| 4,738,139 A | 4/1988 | Blessing et al. | |
| 4,862,383 A * | 8/1989 | Koshimizu et al. ........... 702/39 |
| 4,896,278 A * | 1/1990 | Grove ........................ 702/36 |
| 4,969,361 A | 11/1990 | Kawasaki et al. | |
| 4,991,124 A | 2/1991 | Kline | |
| 5,125,188 A * | 6/1992 | Ogawa et al. ................. 451/5 |
| 5,469,743 A * | 11/1995 | Zorn ........................... 73/627 |
| 5,483,965 A * | 1/1996 | Wiener et al. .............. 600/449 |
| 5,591,913 A * | 1/1997 | Tucker ........................ 73/628 |
| 5,618,994 A * | 4/1997 | Falsetti ....................... 73/602 |
| 5,627,906 A * | 5/1997 | Walach ....................... 382/128 |
| 5,824,908 A * | 10/1998 | Schindel et al. .............. 73/632 |
| 5,852,233 A | 12/1998 | Arnold et al. | |
| 6,182,499 B1 | 2/2001 | McFarland et al. | |
| 6,311,573 B1 * | 11/2001 | Bhardwaj .................. 73/866.5 |
| 6,343,510 B1 * | 2/2002 | Neeson et al. ............... 73/602 |
| 6,367,330 B1 * | 4/2002 | Schafer ....................... 73/598 |
| 6,487,909 B2 * | 12/2002 | Harrold et al. ............... 73/593 |
| 6,581,466 B1 * | 6/2003 | Costley et al. ............... 73/584 |
| 6,606,909 B2 * | 8/2003 | Dubois et al. ............... 73/600 |
| 6,684,704 B1 * | 2/2004 | Obeng ........................ 73/602 |

(Continued)

OTHER PUBLICATIONS

David G. Totzke; "Ultrasound Diagnostic of Chemical Mechanical Planarization Pads"; Aug. 200; pp. 1-62.*

(Continued)

*Primary Examiner*—Hezron Williams
*Assistant Examiner*—Jacques M. Saint-Surin
(74) *Attorney, Agent, or Firm*—Greenberg Traurig LLP; Mauri A. Sankus (57) ABSTRACT

This invention discloses a method of evaluating the internal structure of a grinding wheel through ultrasonic inspection.

18 Claims, 8 Drawing Sheets

U.S. PATENT DOCUMENTS

| | | | |
|---|---|---|---|
| 6,840,108 B2 * | 1/2005 | Stauffer | 73/630 |
| 6,921,321 B2 * | 7/2005 | Morita | 451/60 |
| 6,985,791 B2 * | 1/2006 | Malkin et al. | 700/160 |
| 7,017,414 B2 * | 3/2006 | Falsetti et al. | 73/600 |
| 7,165,451 B1 * | 1/2007 | Brooks et al. | 73/579 |

OTHER PUBLICATIONS

D.G. Totzke et al, "Non-Destructive Characterization of CMP Pads Using Scanning Ultrasonic Transmission"; AIP Conference Proceedings, American Institute of Physics; 2001; pp. 259-262.*

Mahesh C. Bhardwaj et al; "Non-Contact Ultrasound: The Last Frontier in Non-Destructive Testing and Evaluation"; Preprint of a chapter in Encyclopedia of Smart Materials, edited by Mel Schwartz, John Wiley & Sons; Mar. 2002.*

* cited by examiner

METHOD FOR INSPECTING GRINDING WHEELS

CROSS REFERENCE TO RELATED APPLICATIONS

This continuation-in-part application claims the benefit of U.S. application Ser. No. 10/694,649, filed on Oct. 27, 2003 now abandoned, the disclosure of which is fully incorporated by reference herein.

BACKGROUND OF THE INVENTION

1. Field of the Invention

The present invention relates generally to grinding wheels used to grind work rolls used in the production of metal sheet material, such as aluminum sheet. More specifically, the present invention relates to an apparatus and method for inspecting grinding wheels used in the production of metal sheet material.

2. Description of Related Art

A problem in the production of metal sheet material (hereinafter "metal sheet"), such as aluminum sheet, is the introduction of a pattern onto the metal sheet during rolling operations. The "patterning" introduced onto the metal sheet is caused by the work rolls used in rolling operations. The patterning caused by the work rolls is introduced onto the work rolls during preparation of the work rolls for rolling operations. Typically, the work rolls are ground to meet certain pre-established parameters, such as surface roughness, using grinding wheels. Accordingly, if the grinding wheels contain certain defects, these defects are transferred to the work rolls during grinding operations.

As stated, patterning is imprinted onto the work rolls during grinding and is transferred or imprinted onto the metal sheet during rolling operations. Metal sheet containing imprinted patterns is not suitable for sale for surface sensitive products and may be scrapped. The undesired "imprinted" work rolls must then be changed and reground. This results in considerable downtime on the production line and significant monetary loss when a finished metal coil is scrapped.

It is known in the art that for nominally identical grinding wheels some grinding wheels used to prepare work rolls are better to use than others. By better, it is meant that the required work roll roughness specification and other desired parameters may be obtained without introducing patterning onto the work roll, which is then imprinted onto the rolled metal sheet during production. Some grinding wheels cause a great amount of patterning and obtaining the desired roughness specification and other parameters on the work rolls is often difficult or impossible.

Numerous systems and methods are known in the art for generally inspecting the surface quality and other parameters of materials using ultrasound, lasers, and the like. For example, U.S. Pat. No. 6,182,499 to McFarland et al. discloses a method and apparatus for determining the surface quality of an array of materials through the use of acoustical waves. U.S. Pat. No. 5,852,233 to Arnold et al. discloses an acoustic microscope that measures both the typography and elasticity of a material substrate by measuring the deflection of a laser beam. U.S. Pat. No. 4,991,124 to Kline discloses a method for determining the density of a liquid by measuring the amplitude of the reflections of ultrasonic pulses introduced into the liquid. A transducer is used to transmit an ultrasonic pulse through the liquid to a reference material provided in the liquid that is of known density. U.S. Pat. No. 4,969,361 to Kawasaki et al. discloses an ultrasonic device for detecting defects of structural balls. The ball to be tested is provided in a water tank that is filled with water, which is used as the ultrasonic conducting medium. The transducer emits sound waves that are echoed back to the transducer while the ball is rotating in the liquid medium to scan for defects in the ball.

U.S. Pat. No. 4,738,139 to Blessing et al. discloses an ultrasound device that is used to measure surface characteristics such as roughness, scratches, and dents in a substrate. The ultrasound device sends ultrasonic waves through a fluid, which is in laminar flow along a curved path. U.S. Pat. No. 4,603,583 to Heumüller discloses an ultrasonic testing apparatus for testing feritic bodies having a cladding surface. An ultrasound transmitter radiates from a surface opposite the cladding surface into the body at an angle relative to the cladding surface. A receiver receives the reflections emanating from any faults in the body. U.S. Pat. No. 4,364,264 to Re Florentin discloses an ultrasonic device for measuring the degree of roughness of an uneven surface. The ultarsonic device includes a transmitting transducer that propagates sound waves through a liquid coupling medium onto the surface being examined. The ultrasonic device further includes a receiving transducer, which receives reflected waves from the surface being examined.

SUMMARY OF THE INVENTION

While numerous methods and apparatus are known in the art for determining the surface characteristics of a substrate, a need exists in the metal sheet production field to distinguish "good" grinding wheels from "poor" grinding wheels. Additionally, a need exists in the metal sheet production field to objectively identify good versus poor grinding wheels before they are used to prepare work rolls so that patterning is not introduced onto the work rolls and the desired roll surface is created the first and every time a specific grinding wheel is used. Further, a need exists to generally improve upon the production of grinding wheels, thereby improving the quality of work rolls used in metal sheet production. Moreover, a need exists to improve upon the production of metal sheet by decreasing the frequency of patterning during metal sheet production by identifying in advance grinding wheels of known quality.

The foregoing needs are met by the present invention, which is generally directed to a method and system for inspecting grinding wheels used to prepare work rolls used in metal sheet production. In general, the present invention is an ultrasonic inspection system and method for determining variation in density and/or hardness in grinding wheels used to prepare work rolls used in metal sheet production. The ultrasonic grinding wheel inspection system is most preferably a non-contact system wherein sound waves are transmitted through ambient air to the grinding wheel to be inspected. However, a liquid sound conducting medium may be used in the grinding wheel inspection system and method of the present invention.

The sound waves are preferably passed through the body of the grinding wheel to reveal density differences within the grinding wheel. Such density differences are unique for each grinding wheel. For example, the grinding wheel inspection system may include an ultrasonic device or apparatus that passes sound waves through the grinding wheel sequentially from the hub of the grinding wheel to the outer rim of the grinding wheel and vice versa. Density differences are revealed in both the circumferential and radial directions according to the grinding wheel inspection system of the present invention. As the sound waves pass through the grinding wheel the sound waves attenuate. The attenuation is recorded and analyzed by the grinding wheel inspection system to reveal an indicated density profile of the inspected grinding wheel. The indicated density profile is preferably visually displayed on a computer screen to be reviewed by a user of the grinding wheel inspection system, for example as a two or even a three-dimensional image.

The user of the grinding wheel inspection system will review the displayed image to visually inspect the grinding wheel for areas where density differences are pronounced, which is an indication of a poor grinding wheel. For example, the density differences (i.e., indicated density profile) may be displayed as differences in color in the displayed image of the grinding wheel. Different colors may be used to represent different areas of density in the grinding wheel. Any convenient color scheme may be used to distinguish between areas of different density. For example, the color red could be used according to the present invention to represent an area of high density and yellow could be used to represent an area of comparatively lower density. The colors green and blue may be used to represent areas of relatively similar density in the grinding wheel. Any convenient type of color scheme is within the scope of the present invention.

The present invention has as one object to reduce or eliminate the uncertainty surrounding good and poor grinding wheels. As discussed previously, it is known in the art that some grinding wheels are better to use than others in preparing work rolls (i.e., good versus poor grinding wheels). However, prior to the present invention there was no way to objectively differentiate between a good grinding wheel and a poor grinding wheel without actually testing the grinding wheel in a production setting. The process of making a grinding wheel for use in preparing work rolls used in metal sheet production is a well-known process, with numerous steps along the process where inconsistencies in density could be introduced into the grinding wheel. The general process for making a grinding wheel is discussed further herein, as well as the points along the production process where these inconsistencies could be introduced into the grinding wheel. Since these inconsistencies are not currently measured, it is not surprising that grinding wheel users see appreciable variability in grinding performance from one batch of grinding wheels to another as well as within one grinding wheel.

As stated, heretofore, the primary way a defect in a grinding wheel was discovered was the introduction of patterning onto a production run of metal sheet. Once the patterning is revealed, production of metal sheet may have to be halted for roll changes or the metal sheet has to be used for non-surface sensitive applications. If patterning is observed during finish grinding of the work roll, the grinding wheel is typically used until patterning goes away through natural consumption of the grinding wheel during grinding, or the grinding wheel may be "dressed" with a diamond tool to remove the undesired material. If patterning cannot be eliminated through consumption or dressing the grinding wheel may be rejected. The present invention eliminates this inefficient process by identifying the defects before the grinding wheel is used to prepare work rolls and, most importantly, before the work rolls are used in production.

Accordingly, the present invention provides a system and method for inspecting or evaluating the internal structure of grinding wheels and differentiating good grinding wheels from poor grinding wheels. Generally, the method generally comprises rotatably supporting a grinding wheel on a test stand, positioning an ultrasonic transmitting and receiving apparatus proximate to opposite sides of the grinding wheel, rotating the grinding wheel on the test stand, passing sound waves through the grinding wheel, recording amplitude attenuation of the sound waves passing through the grinding wheel to form a histogram, and selecting a subset of the histogram and calculating an average deviation from the mean to evaluate the internal structure of the grinding wheel.

In another embodiment, the method generally comprises supporting the grinding wheel on a test stand, positioning an ultrasonic transmitting and receiving apparatus proximate to opposite sides of the grinding wheel, moving the ultrasonic transmitting and receiving apparatus about the grinding wheel, passing sound waves through the grinding wheel, recording amplitude attenuation of the sound waves passing through the grinding wheel to form a histogram, and selecting a subset of the histogram and calculating an average deviation from the mean to evaluate the internal structure of the grinding wheel.

The ultrasonic transmitting and receiving apparatus may comprise a sound transmitter and sound receiver located proximate to the opposite sides of the grinding wheel, respectively. The step of passing sound waves through the grinding wheel may further comprise passing the sound waves from the sound transmitter to the sound receiver.

The method may further comprise the step of recording amplitude attenuation of the sound waves passing through the grinding wheel. A recording device, such as a digital oscilloscope, or a computer may be used to record the amplitude attenuation. The amplitude attenuation of the sound waves is formed into a histogram, which may be analyzed in the computer to determine indicated density differences through the grinding wheel. In other words, the indicated density differences that are calculated reveal the internal structure of the grinding wheel. Indicated density differences are measured by selecting a subset of the histogram that was formed from the recorded amplitude of the sound waves and calculating an average deviation from the mean. The computer may also so serve as a recording device for recording the amplitude attenuation of the sound waves, as indicated previously. The indicated density differences (i.e. the calculated average deviation from the mean) may be stored as an indicated density profile of the grinding wheel in computer memory. The indicated density profile of the grinding wheel may be displayed on a computer screen for visual inspection. The computer may be programmed to display two or even three dimensional images of the indicated density profile on the computer screen. The indicated density profile is preferably displayed in color to assist the user in determining the internal structure of the grinding wheel. For instance, the indicated density profiles could be displayed in color to assist the user in determining areas of pronounced density differences in the grinding wheel. The indicated density profile of the grinding wheel may be compared with the indicated density profiles of grinding wheels of known operational quality.

The sound waves passed to the grinding wheel are preferably in the range of about 100 KHz to 2 MHz. As indicated previously, the sound waves are preferably passed to the grinding wheel using ambient air as the sound conducting medium.

The system for inspecting grinding wheels according to the present invention generally comprises a test stand adapted to rotatably support a grinding wheel used to prepare work rolls used in metal sheet production, an ultrasonic transmitting and receiving apparatus, and a recording device or computer. In another embodiment, the ultrasonic transmitting and receiving apparatus moves about a stationary grinding wheel. The ultrasonic transmitting and receiving apparatus includes a sound transmitter and sound receiver configured to be positioned proximate to opposite sides of the grinding wheel, respectively. The sound transmitter is adapted to pass sound waves through the grinding wheel that are subsequently received by the sound receiver during operation of the ultrasonic transmitting and receiving apparatus. The recording device or computer is operatively connected to the ultrasonic transmitting and receiving apparatus and is configured to record amplitude attenuation of the sound waves passed through the grinding wheel. Alternatively, the computer may be in operative connection with the recording device for receiving input signals from the recording device indicative of amplitude attenuation of the sound waves passed through the grinding wheel.

The computer may be programmed to analyze the input signals to determine indicated density differences through the grinding wheel and store the indicated density differences as an indicated density profile in computer memory. The computer preferably includes a computer screen for displaying the indicated density profile for visual inspection by the user of the grinding wheel inspection system. The computer may be programmed to display at least a two dimensional image of the indicated density profile on the computer screen. The computer may be further programmed to compare the indicated density profile of an inspected grinding wheel with the indicated density profiles of grinding wheels of known operational quality.

The sound waves generated by the ultrasonic transmitting and receiving apparatus are preferably coupled to the grinding wheel to be inspected using ambient air as the sound conducting medium. The sound waves generated by the sound transmitter and received by the sound receiver of the ultrasonic transmitting and receiving apparatus are preferably in the range of about 100 KHz to 2 MHz.

Further details and advantages of the present invention will become apparent from the following detailed description when read in conjunction with the drawings, wherein like parts are designated with like reference symbols throughout.

DESCRIPTION OF THE PREFERRED EMBODIMENTS

For purposes of the description hereinafter, the terms "upper", "lower", "right", "left", "vertical", "horizontal", "top", "bottom", and derivatives thereof shall relate to the invention, as it is oriented in the drawing figures. However, it is to be understood that the invention may assume many alternative variations and step sequences except where expressly specified to the contrary. It is also to be understood that the specific devices and processes illustrated in the attached drawings and described in the following text are simply exemplary embodiments of the invention. Hence, specific dimensions and other physical characteristics related to the embodiments disclosed hereinafter are not to be considered limiting.

FIGS. 1-4 depict one embodiment of the present invention. The inspection system 10 generally includes a test stand 12. The test stand 12 supports a grinding wheel 14 that is to be inspected for density and/or hardness differences through the grinding wheel 14 that could imprint an undesirable pattern (i.e., "patterning") onto work rolls used in metal sheet production. As indicated previously, grinding wheels are generally known to vary greatly in quality in the field. It is further known in the art that some grinding wheels are better to use than others in preparing work rolls (i.e., "good" versus "poor" grinding wheels). The inspection system 10 and method of testing or inspecting grinding wheels discussed herein provides an objective way or methodology to differentiate between good and poor grinding wheels without actually testing the grinding wheel in a production setting, such as by preparing work rolls and using the work rolls in a production run on metal sheet, such as aluminum metal sheet.

We have discovered that grinding wheels 14 that demonstrate a uniform composition and density variation from hub to rim perform better than those that lack these characteristics in preparing work rolls used in metal sheet production. A high degree of density variation in the internal structure of the grinding wheel 14 indicates that the grinding wheel 14 is of inferior or poor quality. In other words, if the subset of the histogram that is selected has a large deviation from the mean, then the grinding wheel 14 is of inferior or poor quality. In FIGS. 1-4, the hub of the grinding wheel 14 is designated with reference numeral 16 and the rim of the grinding wheel 14 is designated with reference numeral 18. We have discovered that a "good" grinding wheel 14 will have a substantially uniform density in the circumferential direction (i.e., concentrically from the hub 16 to the rim 18). In the case of a "good" grinding wheel, the subset of the histogram that is selected would have a small deviation from the mean. Circumferential uniformity is of the greatest importance since it most greatly effects introduction of pattern during the grinding process Any areas within the grinding wheel 14 where density changes abruptly or is pronounced is undesirable because these distinct density differences are likely to introduce patterning onto the work rolls that are prepared using the grinding wheel 14 and, ultimately, the metal sheet rolled using the work rolls. The transition between areas of pronounced density differences is the likely cause of imprinting patterning onto work rolls and, ultimately, a production run of metal sheet material.

In one embodiment, the test stand 12 is adapted to rotatably support the grinding wheel 14 to be inspected, preferably along a vertical axis as illustrated in FIGS. 1-4. However, the test stand may also be adapted to support the grinding wheel 14 along a horizontal axis, or along another axis as desired. The test stand 12 may be conventional in the art. The inspection system 10 further includes an ultrasonic transmitting and receiving apparatus 20 located proximate to the test stand 12 and grinding wheel 14 to be inspected. The ultrasonic transmitting and receiving apparatus 20 is mounted on an arm 22, which is further connected to a pedestal or base 24 that supports the ultrasonic apparatus 20. The pedestal 24 is preferably height-adjustable so that the ultrasonic apparatus 20 may be adjusted to the height of the grinding wheel 14 on the test stand 12. Additionally, the ultrasonic apparatus 20 is preferably movably mounted on the arm 22 so that it may move sequentially form the hub to rim 16, 18 and vice versa, as discussed further herein, to inspect the density variations in grinding wheel 14 in the circumferential direction.

Figure 2:
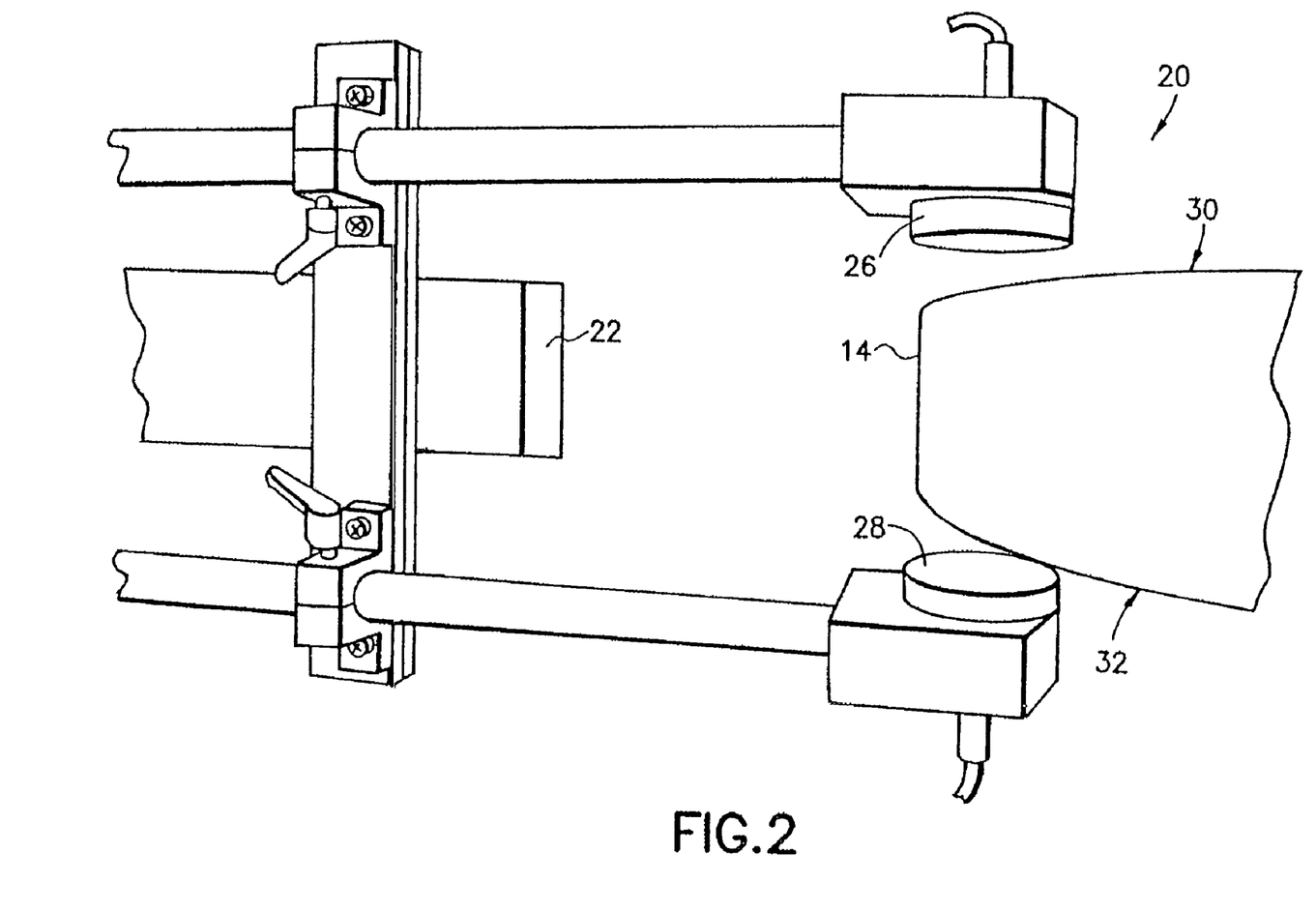
FIG. 2 is a perspective view of an ultrasonic transmitting and receiving apparatus used in the grinding wheel inspection system of FIG. 1.
Figure 3:
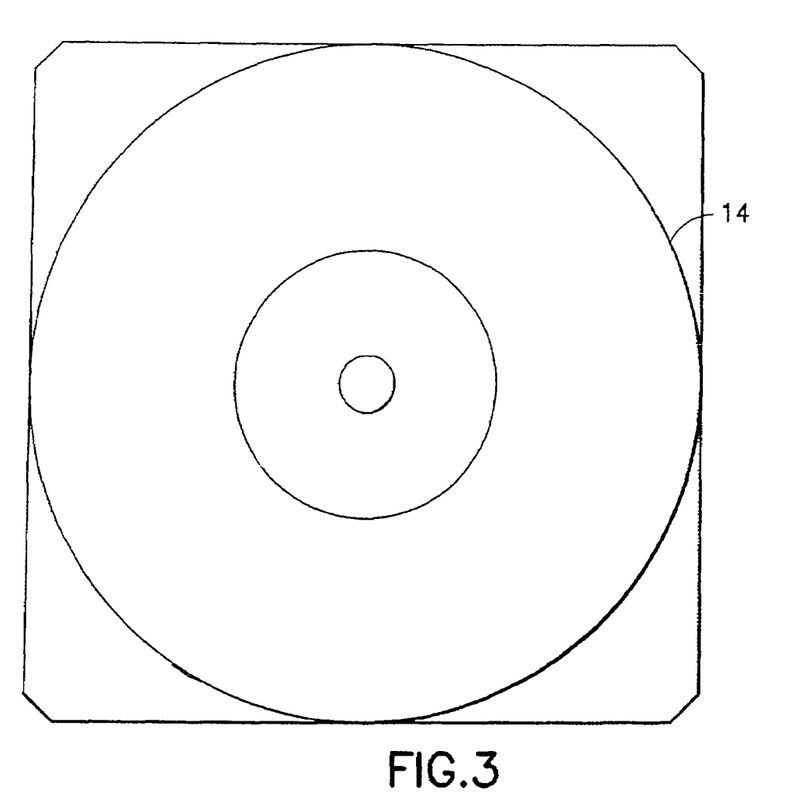
FIG. 3 is a plan view of a suitable test stand for use in the grinding wheel inspection system of FIG. 1.
Figure 4:
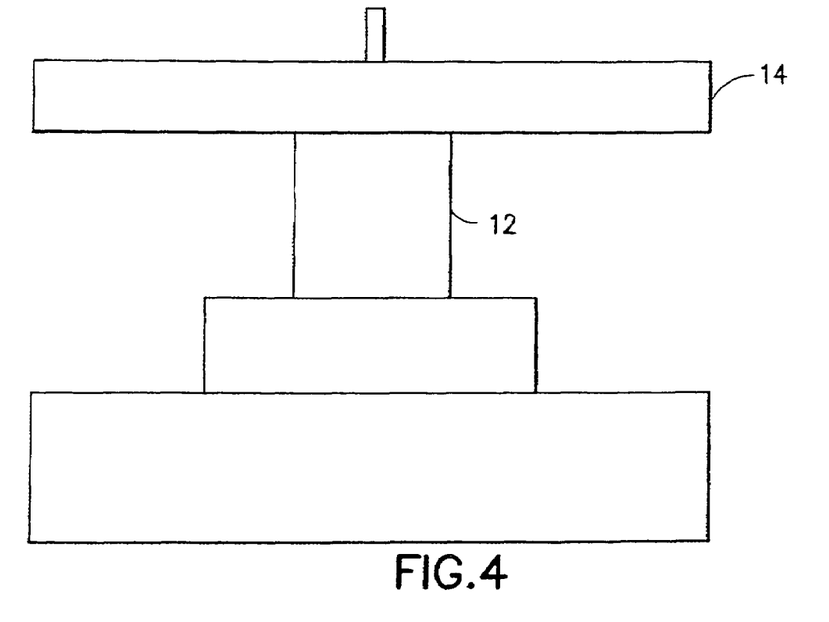
FIG. 4 is a side elevational view of the test stand of FIG. 3, shown supporting a grinding wheel to be inspected.

The ultrasonic apparatus includes a sound transmitter 26 and a sound receiver transducer 28 that are adapted to be positioned proximate to opposite sides 30, 32 of the grinding wheel 14, as illustrated most clearly in FIG. 2. The sound transmitter 26 and sound receiver 28 may be conventional devices known in the art and are adapted to pass sound waves through the grinding wheel 14. Suitable transmitters/receivers for the sound transmitter 26 and sound receiver 28 are manufactured by Ultran Industries. In particular, the sound transmitter 26 is adapted to conduct sound waves to the top face or side 30 of the grinding wheel 14, which pass through the grinding wheel 14 to be received by the sound receiver 28 located proximate to the bottom face or side 32 of the grinding wheel 14. Preferably, the sound transmitter 26 is configured to transmit and the sound receiver 28 is configured to receive sound waves in the range of about 100 KHz to 2 MHz.

The sound transmitter 26 and sound receiver 28 are preferably movably mounted on the arm 22, as indicated. In operation, the sound transmitter 26 and sound receiver 28 are preferably movable from the hub 16 to the rim 18 of the grinding wheel 14, or vice versa, so that the entire area between the hub 16 and rim 18 is examined by the ultrasonic apparatus 20 as the grinding wheel 14 rotates on the test stand 12. This sequential movement ensures that radial as well as circumferential density variations are examined by the ultrasonic apparatus 20. The movement of the sound transmitter 26 and the sound receiver 28 on the arm 22 is preferably controlled by a control device such as a computer as discussed herein.

The sound waves emitted by the sound transmitter 26 are transferred to the top face or side 30 of the grinding wheel using ambient air as the sound conducting medium. The sound waves pass through the body of the grinding wheel 14 to be received by the sound receiver 28. The sound waves attenuate as they pass through the body of the grinding wheel 14, revealing the internal structure of the grinding wheel 14. The internal structure of the grinding wheel 14 may then be examined for variations in density and/or hardness. A pronounced difference in density from one area of the grinding wheel 14 to another and/or a great deal of density variation within the grinding wheel 14 are indicative of a grinding wheel 14 that is likely to perform poorly in preparing work rolls for use in metal sheet production, for example aluminum sheet production. The variations in density revealed by the attenuation in the sound waves passed through the grinding wheel 14 are most effectively analyzed and displayed by a computer. Accordingly, a computer 34 is in operative connection with the ultrasonic apparatus 20.

The computer 34 includes a computer screen 36 for displaying an image representing density and/or hardness differences in the inspected or tested grinding wheel 14, as indicated by the ultrasonic apparatus 20. A suitable computer for the present invention is manufactured by eIndustrial Computer Inc. In a preferred embodiment, the computer 34 is operatively connected directly to the ultrasonic apparatus 20 and the data is transferred digitally between these units. Alternatively the sound wave attenuation may be transferred in analog form and recorded by a digital oscilloscope or a suitable analog to digital converter, A/D, which serves as a recording device 38 for the. The oscilloscope data is transferred to the computer 34 after each scan line is completed. If an A/D converter is used, the data can be buffered or transmitted to the computer 34 point-by-point.

In operation, the computer 34 receives input signals from the recording device 38 or directly from the ultrasonic apparatus 20 representative of the sound wave attenuation and, more particularly, variations in sound wave attenuation caused by the internal structure of the grinding wheel 14 under examination. The computer 34 is generally programmed to analyze the input signals and display the variations in sound wave attenuation as a visual image on the computer screen 36. The visual image is representative or indicative of the differences in density and/or hardness in the grinding wheel 14. As stated above, the indicated densities are measured by selecting a subset of the histogram, which is a compilation of the recorded amplitude attenuations, and calculating an average deviation from the mean. The computer 34 may be programmed to assign a color scheme to the indicated density differences within the grinding wheel 14, referred to hereinafter as an "indicated density profile" 40 of the inspected grinding wheel 14, as discussed further herein. As will be appreciated by those skilled in the art, the indicated density profile 40 will be unique for each grinding wheel 14 tested or inspected and is analogous to a "fingerprint" for the grinding wheel 14. The displayed indicated density profile 40 is not the actual density of the inspected grinding wheel 14, but rather is a representation of density or, more particularly, a representation of density differences within the inspected grinding wheel 14.

Referring to FIGS. 1-5, the general procedure for testing or inspecting and evaluating a given grinding wheel 14 will now be discussed. To test a given grinding wheel 14, the grinding wheel 14 is placed on the test stand 12, which is adapted to rotate the grinding wheel 14 about a vertical axis while the ultrasonic apparatus 14 passes sound waves through the body of the grinding wheel 14. The ultrasonic apparatus 14 is placed in close proximity to the grinding wheel 14 to be inspected and evaluated. In particular, the sound transmitter 26 is placed proximate to or opposite the top face or side 30 of the grinding wheel 14, and the sound receiver 28 is placed proximate to or opposite the bottom face or side 32 of the grinding wheel 14. It will be appreciated by those skilled in the art that the locations of the sound transmitter 26 and sound receiver 28 may be reversed. The ultrasonic apparatus 20 may be in operative connection with the recording device 38 or, more preferably, directly connected to the computer 34, which thus serves as the recording device as discussed previously. The ultrasonic apparatus 20 itself includes an embedded computer that acquires the data and transmits that data to the computer 34 or recording device 38. The embedded computer controls the scanning operation and triggers the ultrasonic apparatus 20 to acquire and exchange data.

The computer 34 is further preferably used to control the movement of the sound transmitter 26 and sound receiver 28 which are movably mounted on the arm 22. In particular, the computer 34 preferably controls the movement of the sound transmitter 26 and sound receiver 28 on the arm 22 so that the sound transmitter 26 and sound receiver 28 sequentially and in tandem move from the rim 18 of the grinding wheel 14 to the hub 16 of the grinding wheel 14, or vice versa, while the grinding wheel 14 is rotating on the test stand 12. The computer 34 may further control the starting and termination of sound waves emanating from the sound transmitter 26 and received by the sound receiver 28 to coincide with the movement of sound transmitter 26 and sound receiver 28 from the rim 18 to the hub 16 of the grinding wheel 14 to be inspected, or vice versa.

Figure 5:
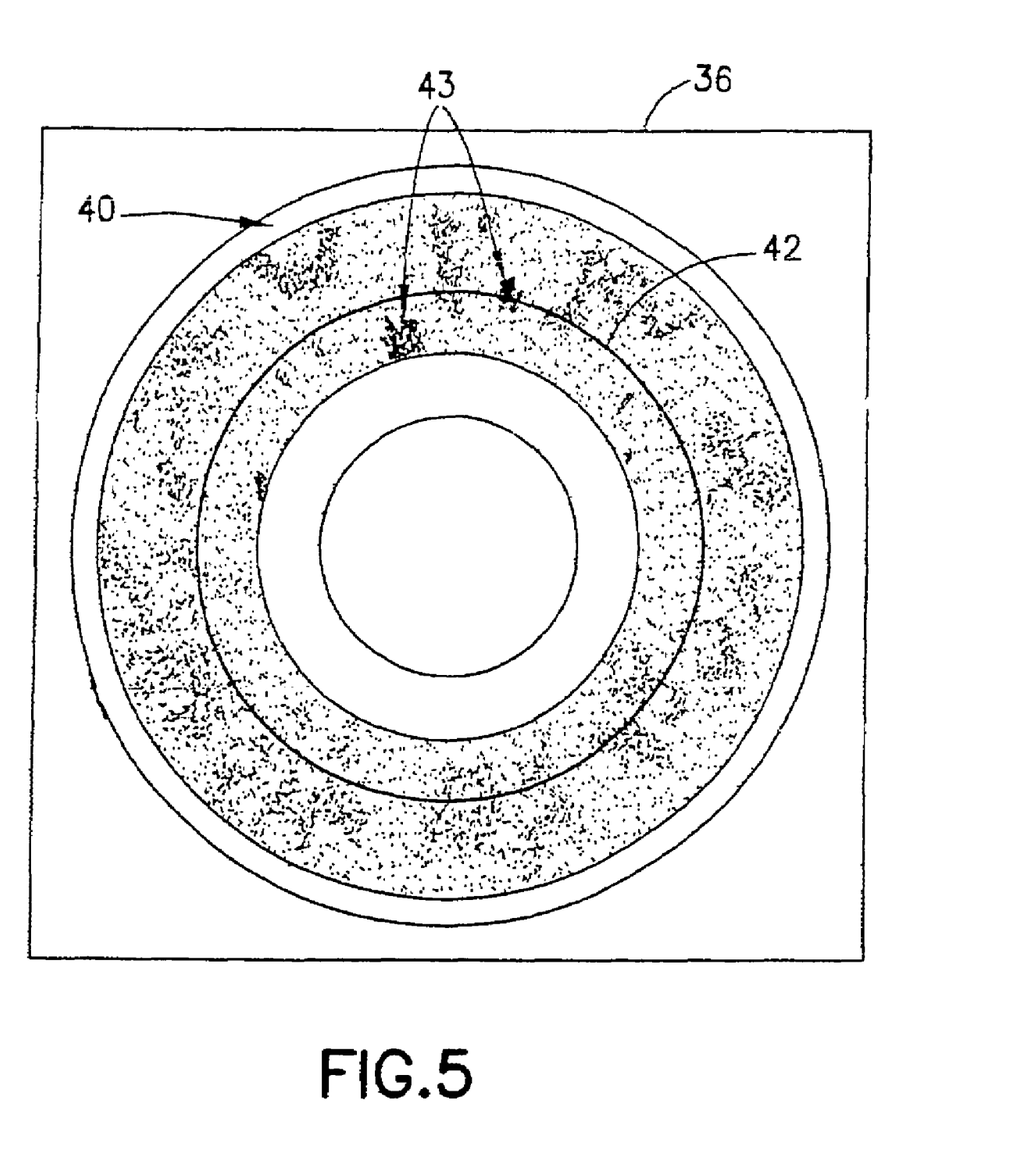
FIG. 5 is an exemplary computer display showing an indicated density profile of an inspected grinding wheel.

As the grinding wheel 14 is rotated on the test stand 12, the sound transmitter 26 transmits sound waves to the top face 30 of the grinding wheel 14. The sound waves pass through the body of the grinding wheel 14 to be received by the sound receiver 28 located proximate to the bottom face or side 32 of the grinding wheel 14. In the body of the grinding wheel 14, the sound waves attenuate as the sound waves pass through the grinding wheel 14. The sound transmitter 26 and sound receiver 28 as they move in tandem from, for example, the rim 18 to the hub 16 of the grinding wheel 14 capture concentric circles of data points representing concentric "slices" of the grinding wheel 14. In FIG. 5, one of the concentric data point circles is shown and is represented by reference numeral 42, which is generally used to designate any concentric data point circle referred to in this disclosure. Any number of concentric data point circles 42 may be taken by the ultrasonic apparatus 20 and communicated to the recording device 38 and/or computer 34.

The attenuation of the sound waves in the body of the grinding wheel 14 is related to density and/or hardness changes in the grinding wheel 14. In particular, the attenuation in amplitude of the sound waves in the body of the grinding wheel 14 is related to density and/or hardness changes in the grinding wheel 14. The amplitude attenuation is recorded over a discrete time period by the recording device 38 or by the computer 34 itself. It is the amplitude attenuation and variations thereof that gives the indication of density differences through the grinding wheel 14. As stated in the paragraphs above, indicated density difference is measured by selecting a subset of the histogram, which is a compilation of the recorded amplitude attenuations, and calculating an average deviation from the mean. A large deviation from the mean suggests that the grinding wheel 14 is of an inferior or "poor" quality, while a small deviation from the mean suggests that the grinding wheel 14 is of adequate or "good" quality.

The ultrasonic apparatus 20 provides the concentric "slices" or concentric data point circles 42 as input signals (i.e. data points) to the recording device 38, or to the computer 34 directly, where the concentric slices or concentric data point circles 42 are recorded. Initially, the input signals consist of decibel (dB) values at each inspection point. The inspection point is where a sound wave is passed through the grinding wheel 14 and the amplitude attenuation of the sound wave is recorded. These input signals are typically displayed as a spectrum having peaks of various heights on the computer screen 36. As indicated, any number of concentric data point circles 42 may be taken by the ultrasonic apparatus 20 and communicated to the recording device 38 or computer 34. It will be appreciated by those skilled in the art that the greater number of concentric data point circles 42 taken by the ultrasonic apparatus 20 from the hub 16 to the rim 18 and vice versa, the more enhanced and accurate the indicated density profile 40 of the grinding wheel 14 will ultimately be. The concentric data point circles 42 are equally spaced and are used to form a database of polar coordinates that fully encompasses the usable surface area of the wheel 14.

The recorded concentric data point circles 42 are preferably provided as input signals to the computer 34 from the recording device 38, or are recorded directly in the memory of the computer 34. The computer 34 is then used to evaluate or analyze the recorded data. This is done by selecting a primary peak from the recorded spectrum that is displayed on the computer screen 36 and forming a histogram from the primary peak. Typically, the primary peak is selected since it has the highest signal-to-noise ratio, which allows for a more accurate reading of the internal structure of the grinding wheel 14. A subset of the histogram is then selected and an average deviation from the mean is calculated in order to evaluate the grinding wheel 14. As stated in the preceding paragraphs, a large deviation from the mean suggests that the grinding wheel 14 is of an inferior or "poor" quality, while a small deviation from the mean suggests that the grinding wheel 14 is of adequate or "good" quality.

The recorded concentric data point circles 42 are preferably provided as input signals to the computer 34 from the recording device 38, or are recorded directly in the memory of the computer 34. The computer 34 is then used to evaluate or analyze the recorded data. This is done by selecting a primary peak from the recorded spectrum that is displayed on the computer screen 36 and forming a histogram 50 from the primary peak. Typically, the primary peak is selected since it has the highest signal-to-noise ratio, which allows for a more accurate reading of the internal structure of the grinding wheel 14. A subset of the histogram is then selected and an average deviation from the mean is calculated in order to evaluate the grinding wheel 14. As stated in the preceding paragraphs, a large deviation from the mean suggests that the grinding wheel 14 is of an inferior or "poor" quality, while a small deviation from the mean suggests that the grinding wheel 14 is of adequate or "good" quality.

Any convenient color scheme may be used to distinguish between areas of different density. For example, the color red could be used according to the present invention to represent an area of indicated high density (i.e. a large deviation from the mean) and yellow could be used to represent an area of comparatively low indicated density (i.e. a small deviation from the mean). The colors green and blue, for example, may be used to represent areas of relatively similar indicated density (i.e. substantially similar deviation from the mean) in the grinding wheel 14. Any convenient type of color scheme is within the scope of the present invention and it is within the skill of those skilled in the art to develop an appropriate color scheme for the indicated density profile 40. In one embodiment, the histogram can be manipulated using a click and drag graphic user interface (GUI) in a manner that allows for instantaneous contrast enhancements, color shifting, and scaling of the indicated density profile 40 that is being displayed on the computer screen 36. In another embodiment, the colors that are used in the indicated density profile 40 may be inverted if desired.

Any number of data points may make up the concentric data point circles 42. However, the same number of data points is preferably taken for each concentric data point circle 42. Thus, the concentric data point circles 42 located near the hub 16 of the grinding wheel 14 have the same number of data points as the concentric data point circles 42 located farther out near the rim 18. In one embodiment, 1000 equally spaced measurements are made for each concentric data point circle 42. The computer 34 is programmed to provide a uniform image on the computer screen 38 of the indicated density profile 40 even though the spacing between data points will vary in each concentric data point circle 42. The computer 34 is programmed to linearly shade between each data point in the concentric data point circle 42 to form a solid image regardless of the spacing distance between the data points. A Gouraud shading model may be utilized for this purpose, such that all pixels in the image of the grinding wheel 14 displayed on the computer screen 38 represent the best estimate or representation of ultrasonic sound wave attenuation, preferably amplitude attenuation, at all points within the inspected grinding wheel 14. The Gouraud shading model is known to those skilled in the art.

Figure 1:
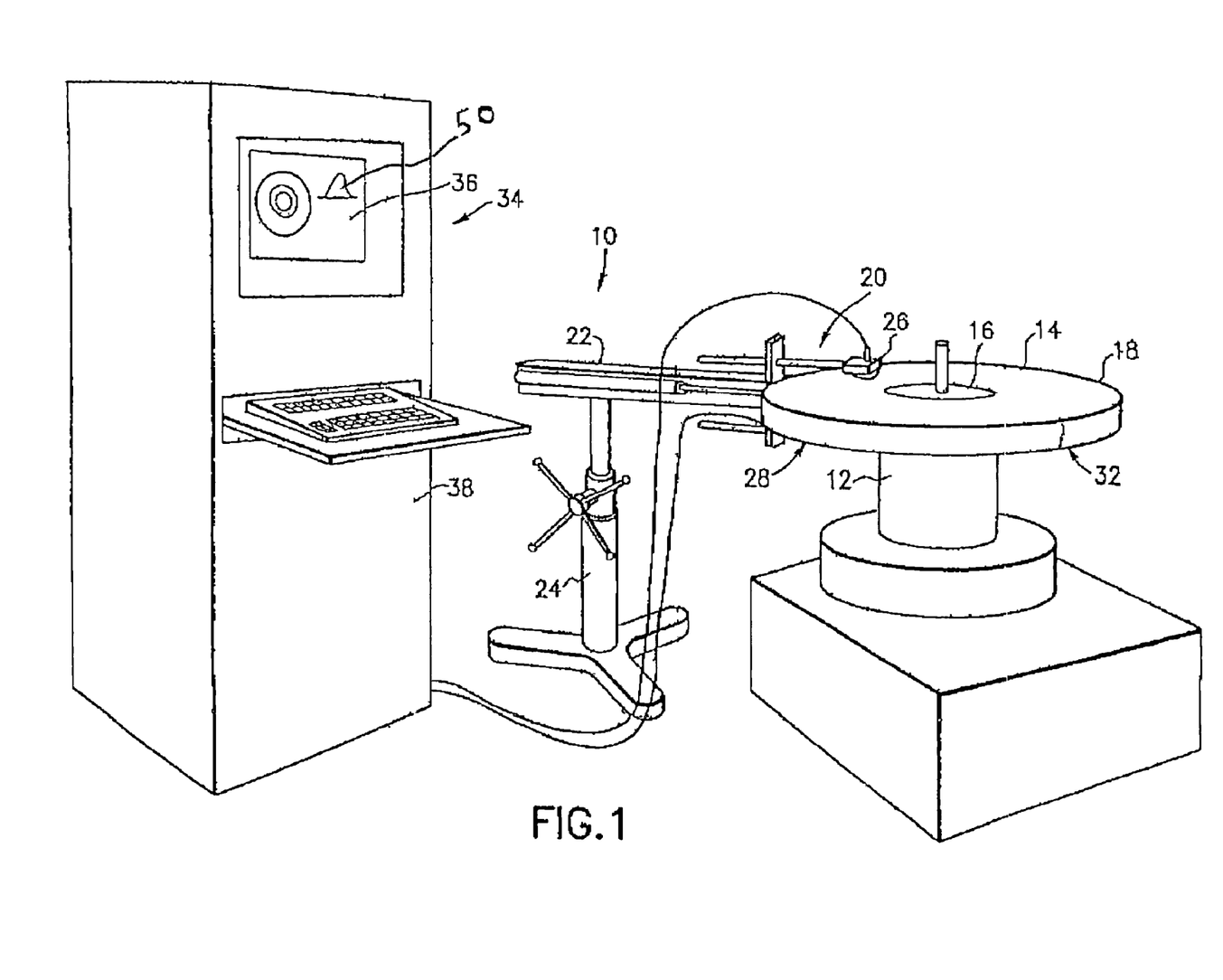
FIG. 1 is a perspective view of a system for inspecting grinding wheels in accordance with the present invention.

In summary, the computer 34 is operatively connected to the recording device 38, or itself serves as a recording device to receive input signals from the ultrasonic apparatus 20. In FIG. 1, reference number 38 is assigned to the location in the computer 34 hardware support structure where the recording device 38 may be situated. The computer 34 uses the recorded concentric data point circles 42 to electronically construct a visual representation of the interior of the inspected grinding wheel 14 (i.e., the indicated density profile 40 of the grinding wheel 14). The indicated density profile 40 is an image representing the density differences within the grinding wheel 14 rather than an actual value of the density or density differences within the grinding wheel 14. As stated in the preceding paragraphs, indicated density difference is measured by selecting a subset of the histogram, which is a compilation of the recorded amplitude attenuations, and calculating an average deviation from the mean. In particular, the computer 34 takes the individual concentric data point circles 42 taken by the ultrasonic device 20 and compiles an image representing an "indicated" density cross section or "profile" 40 of the grinding wheel 14. Preferably, the displayed image uses colors to differentiate between areas of different density within the grinding wheel 14.

Unlike current ultrasound transmission methods, the grinding wheel inspection apparatus 10 and method of the present invention utilizes air as the sound transmitting medium for the sound transmitter 26 and sound receiver 28. Conventional ultrasonic devices typically rely on liquids as the sound conducting medium.

The present invention is concerned with providing an objective procedure for evaluating grinding wheels 14 before they are used to prepare work rolls. More particularly, the present invention is intended to provide a simple and effective method of identifying poor quality grinding wheels 14 before they are used to prepare work rolls and, more importantly, before the work rolls are used on a production run of metal sheet. As mentioned previously, grinding wheels 14 are typically fabricated using a "cookbook" or recipe style of manufacturing, which is primarily concerned with grit size, grit distribution, binders, etc. This type of manufacturing process is believed to be a significant factor of introducing "hard spots" or "soft spots" into a grinding wheel. These "hard spots" or "soft spots", which are areas of pronounced density differences within a grinding wheel 14, are believed to be the root cause of imprinting "patterning" onto work rolls, which is then transferred to metal sheet during rolling operations. The present invention is thus further concerned with improving the manufacturing process of grinding wheels 14 to reduce defects that could cause patterning on work rolls.

The "cookbook" style of manufacturing the grinding wheel 14 is well known in the art and generally follows the following step sequence. Initially, the components of the grinding wheel 14 are weighed and measured according to a prescribed recipe. These components include abrasive grit, binding agents, and additives. The components are mixed in a mixer for a set period of time and are sieved as need to exclude large clumps of material. The mixture is then poured into a mold, which may be a stationary or rotating mold. A stirring knife is used in the mold as necessary. Vibration may also be applied to the mold as needed to settle material. A mold top may press the in situ material that will form the grinding wheel 14 to press the in situ material to proper dimensions. Once the molding process in complete, the grinding wheel 14 is removed from the mold in a "green" state and dried to remove moisture, such as in a low temperature furnace. The grinding wheel 14 may be sintered in a high temperature furnace as necessary and machined to required dimensions and balanced.

The inspection system 10 and method of the present invention may be applied to the foregoing manufacturing process to improve the manufacturing process. Currently, defects are known to be introduced into the grinding wheel 14 at several points along the manufacturing process. For example, density differences within the grinding wheel 14 are known to be caused by inadequate mixing during the mixing step, by allowing the components of the grinding wheel 14 to settle out or separate within the mold during the pouring and in situ curing step, and by non-uniform pressing of the material in the mold. The inspection system 10 and method of the present invention may be used to identify points along the manufacturing process where the process and the resulting quality of the finished grinding wheel 14 could be improved. For example, the grinding wheel 14 could be inspected while in the "green" state before being dried in a furnace. Thus, poor quality grinding wheels 14 may be identified prior to the final finishing steps for the grinding wheel 14 saving production costs. Rejected "green" state grinding wheels 14 could be recycled for their raw materials, further saving costs in the manufacturing process.

Additionally, the results of the inspection process could be used to identify mixing, mold-filling and curing, and mold-pressing problems to improve the manufacturing process as whole. The results of the inspection process could be used, for example, to optimize mixing, mold-filling, and mold-pressing in accordance with the present invention, or to correct systemic errors that may be occurring in the production process and resulting in poor quality grinding wheels 14. For example, once a "poor" grinding wheel 14 is identified by the process described previously, the results of the inspection could be analyzed to determine what type of specific defects are present in the grinding wheel 14 and where along the manufacturing process the defects were most likely introduced into the grinding wheel 14. If a consistent pattern becomes apparent from inspecting multiple grinding wheels 14 made by the same manufacturer, for example repeated problems associated with inadequate mixing the material comprising the grinding wheel 14, the manufacturer could be alerted to inspect their equipment for defects. The foregoing is just one non-restrictive example of how the present invention could be applied to improve the manufacturing process for grinding wheels 14 generally. Other specific examples are discussed in connection with FIGS. 5-9, discussed herein.

Referring to FIG. 5-9, the indicated density profiles 40 of specific and actual grinding wheels 14 inspected using the methodology and inspection system 10 of the present invention are shown. FIG. 5 illustrates an indicated density profile 40 wherein darker areas of the indicated density profile 40 are representative of areas of higher density and lighter areas of the indicated density profile 40 are representative of areas of comparatively lower density. The indicated density profile 40 depicted in FIG. 5 shows that density is not substantially uniform within the inspected grinding wheel 14 but also does not indicate the presence of a major defect or flaw. The indicated density profile 40 of FIG. 5 indicates that the inspected grinding wheel 14 is of intermediate quality. The indicated density profile 40 of FIG. 5 shows two darker areas representing areas of substantially increased density 43, one lying along the concentric data point circle 42 and another adjacent the hub of the grinding wheel 14 at about the 90° position of the grinding wheel 14. As the surface of the grinding wheel 14 is consumed during work roll grinding operations, the higher density area 43 lying on/near the concentric data point circle 42 in FIG. 5 could be a concern as a "hard spot" of increased density relative to adjacent areas of the grinding wheel 14. Such a "hard spot" could cause patterning on work rolls prepared by the grinding wheel 14, as discussed previously.

Figure 6:
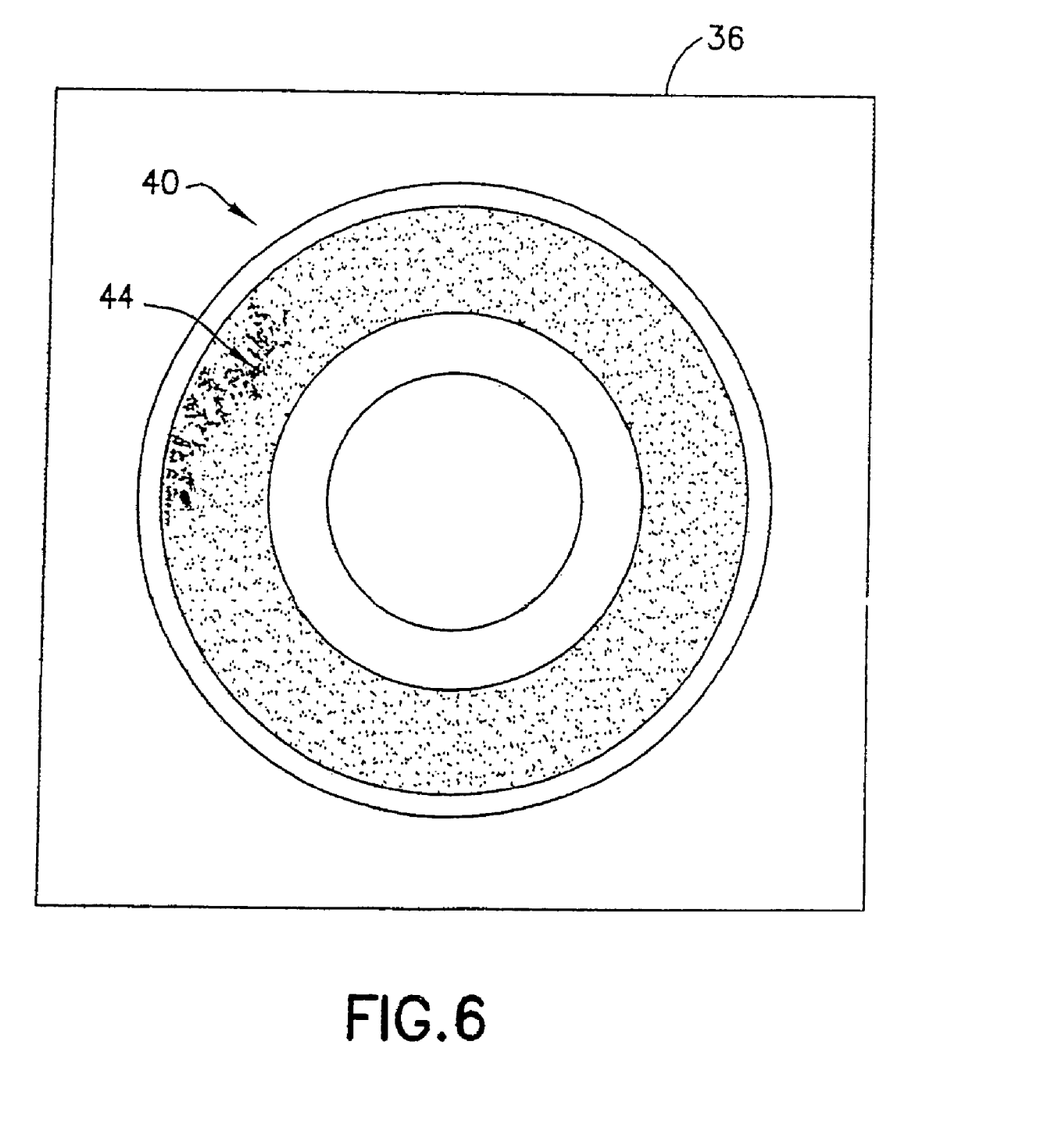
FIG. 6 is a computer display showing an indicated density profile of an inspected grinding wheel, wherein indicated density differences are pronounced in one quadrant of the inspected grinding wheel.

FIG. 6 illustrates an indicated density profile 40 for an inspected grinding wheel 14, wherein a large area of substantially increased density 44 is present in one quadrant of the grinding wheel 14. The area of substantially increased density 44 is considerably darker than the other portions or areas of the grinding wheel 14, which are of relatively uniform density as represented by the relatively uniform shading in the other three quadrants of the grinding wheel 14. Accordingly, the indicated density profile 40 of FIG. 6 indicates that the inspected grinding wheel 14 is of inferior or poor quality. This is due to the presence of the large area of substantially increased or pronounced density 44 in comparison with the remainder of the grinding wheel 14. The differences in density present within the inspected grinding wheel 14 and, more particularly, the concentrated difference in the upper left quadrant of the grinding wheel 14 is likely to imprint patterning on work rolls prepared with the grinding wheel 14.

Figure 7:
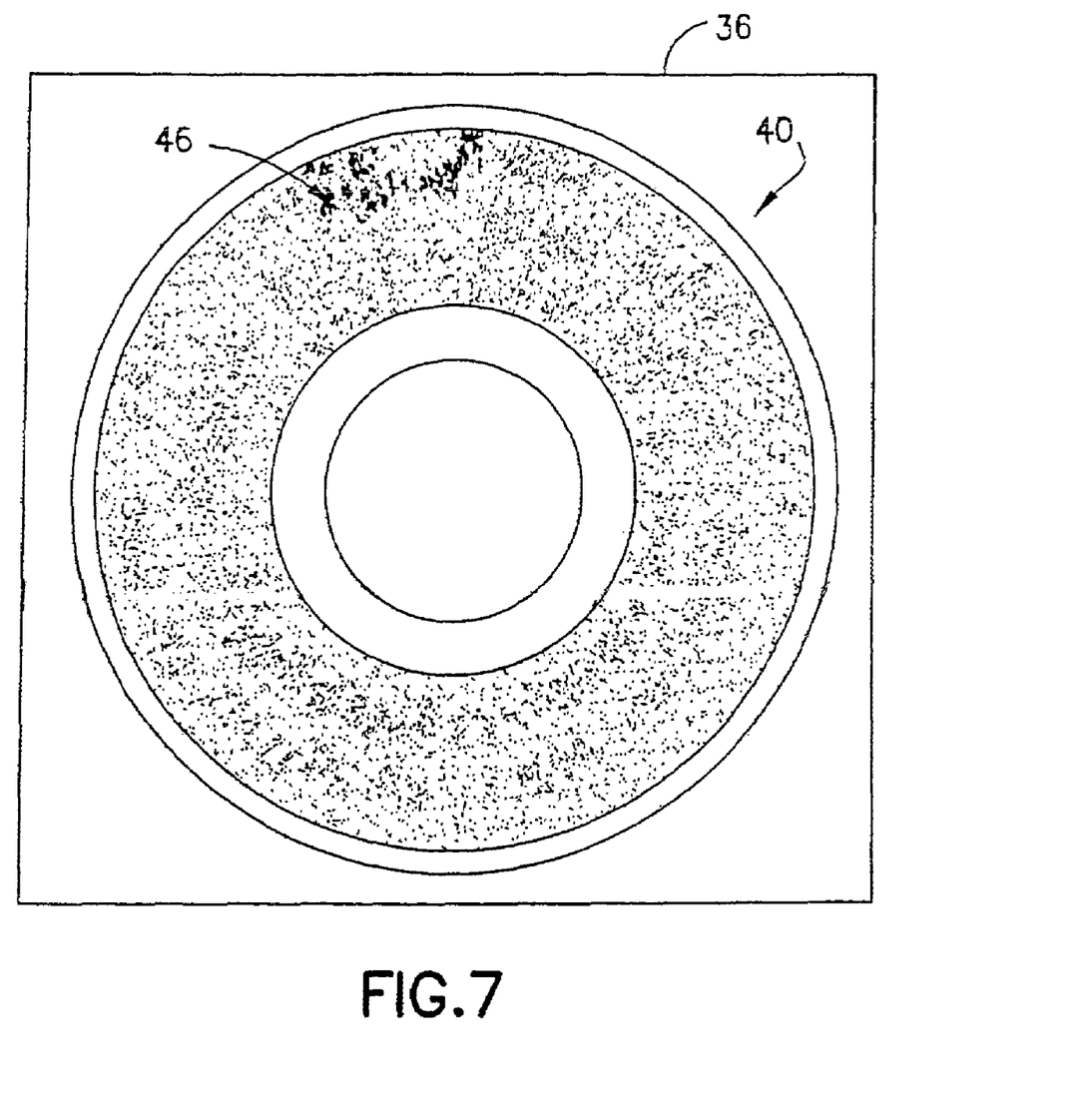
FIG. 7 is a computer display showing an indicated density profile of an inspected grinding wheel, wherein the indicated density profile indicates that the inspected grinding wheel was injected with additional material during formation.

FIG. 7 likewise illustrates an indicated density profile 40 for an inspected grinding wheel 14 of poor overall quality. The indicated density profile 40 illustrated in FIG. 7 shows that a large area of substantially increased density 46 is present in a localized area of the inspected grinding wheel 14, substantially near the rim of the grinding wheel 14. The area of substantially increased density 46 is considerably darker than the other portions or areas of the grinding wheel 14, which are again of relatively uniform density as represented by the relatively uniform shading in the indicated density profile 40. Variations in density are indicated by the indicated density profile 40 outside of the areas of substantially increased density 46, but these variations are not distinct or pronounced through the grinding wheel 14. The area of substantially increased or pronounced density 46 is indicative of additional material being injected into the grinding wheel 14 during manufacturing. It is likely the additional material was injected into the grinding wheel 14 during the balancing step, which is one of the final finishing steps for the grinding wheel 14. The concentrated density difference present in one area of the inspected grinding wheel 14 and, more importantly, near the rim of the grinding wheel 14 is likely to imprint patterning on work rolls prepared with the grinding wheel 14 depicted in FIG. 7.

Figure 8:
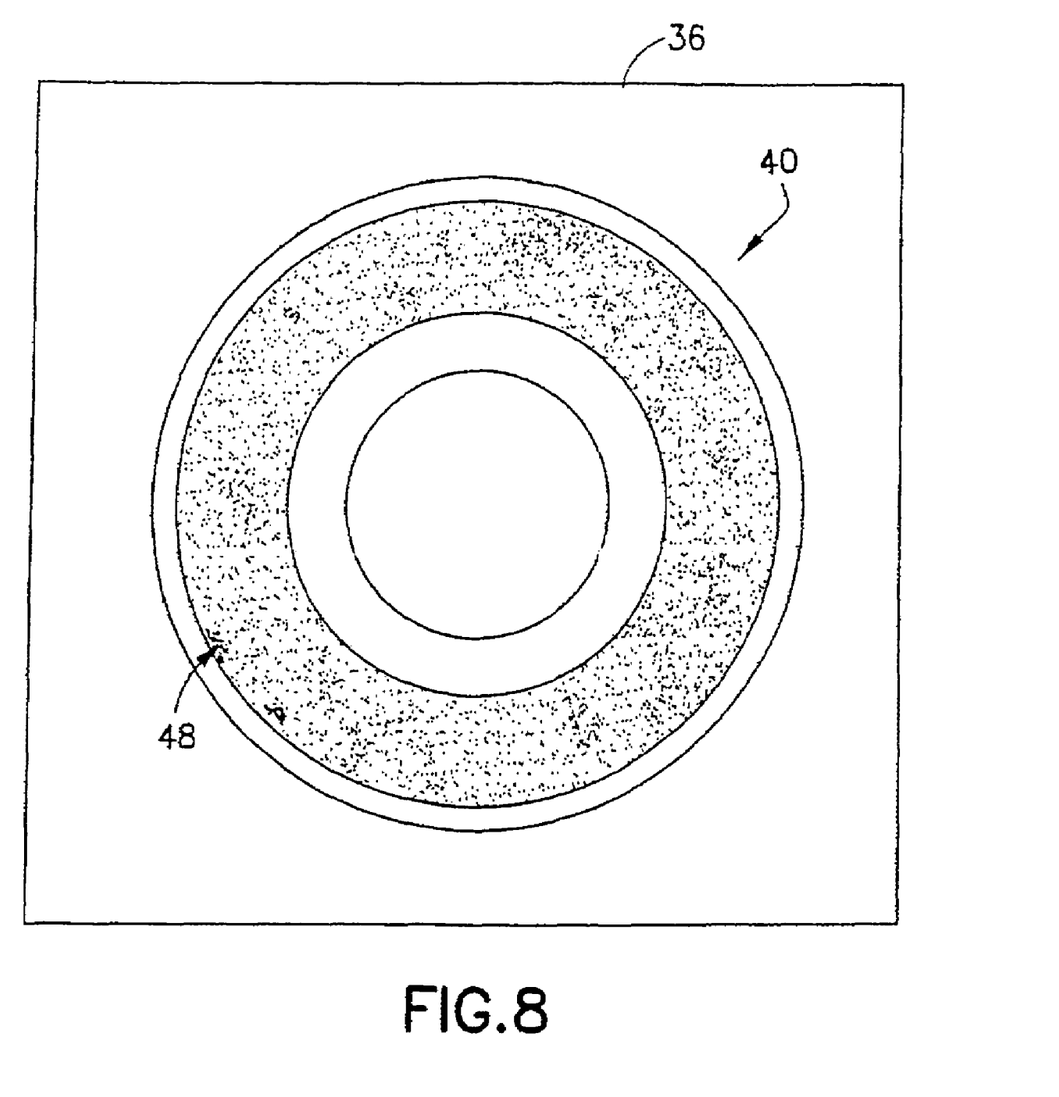
FIG. 8 is a computer display showing an indicated density profile of an inspected grinding wheel, wherein the indicated density profile indicates a potential radial crack in the inspected grinding wheel.

FIG. 8 illustrates an indicated density profile 40 for an inspected grinding wheel 14 that is also of poor overall quality. The indicated density profile 40 illustrated in FIG. 8 shows the presence of a possible radial crack 48 substantially near the rim of the grinding wheel 14. The possible radial crack 48 is revealed as a dark area in comparison to other portions or areas of the grinding wheel 14, which are again of relatively uniform density as represented by the relatively uniform shading in the indicated density profile 40. Again, variations in density are indicated by the indicated density profile 40 outside of the area containing the possible radial crack 48, but these variations are not distinct or pronounced through the grinding wheel 14. The possible radial crack 48 could have occurred during the manufacturing process or during use. For example, the possible radial crack 48 could have occurred during curing of the "green" state grinding wheel 14, during final machining, or during use of the grinding wheel 14 in grinding operations. The possible radial crack 48 lies near the rim of the grinding wheel 14 and is likely to imprint patterning on work rolls prepared with the grinding wheel 14 illustrated in FIG. 8.

Figure 9:
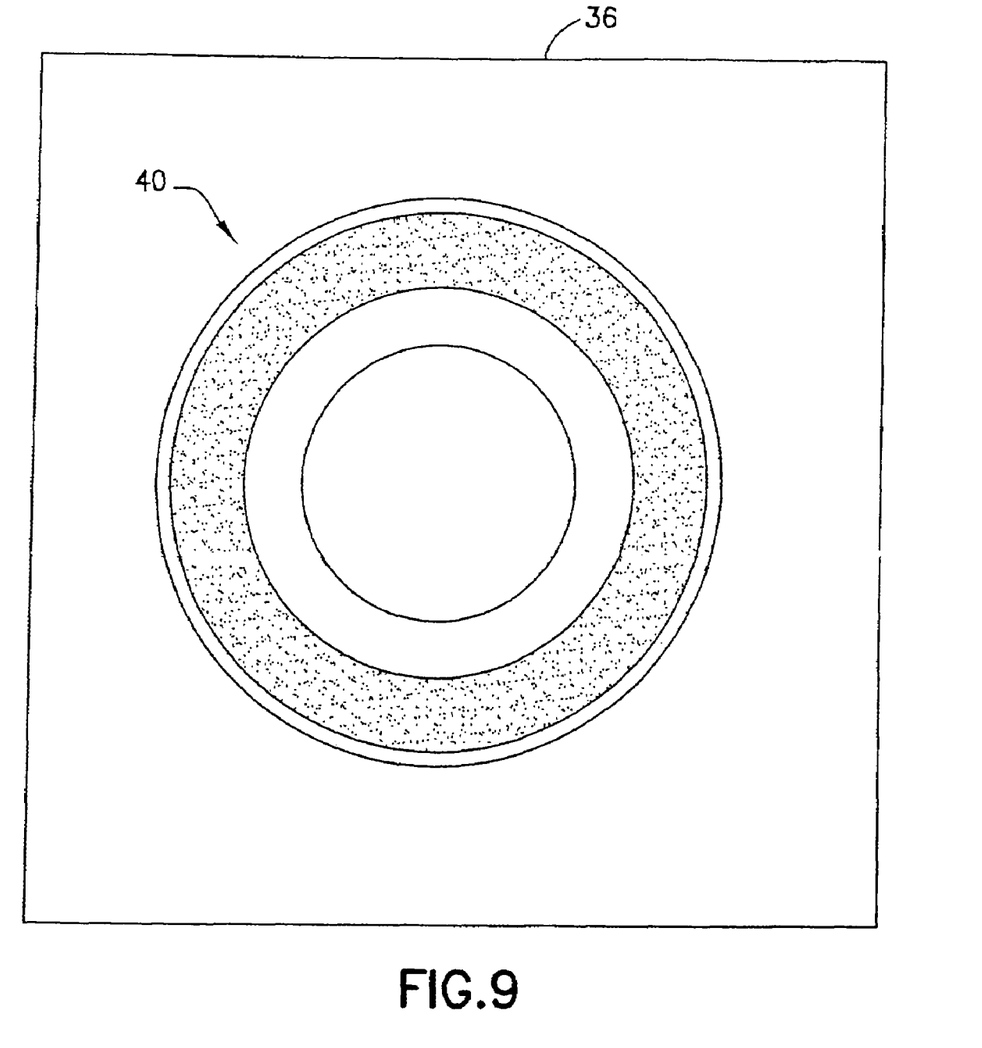
FIG. 9 is a computer display showing an indicated density profile of an inspected grinding wheel of indicated good quality.

In contrast to FIGS. 5-8, FIG. 9 illustrates an indicated density profile 40 for an inspected grinding wheel 14 of good quality. In FIG. 9, the indicated density profile 40 shows an absence of "hard spots" or "soft spots", or areas of pronounced or increased density relative to other areas of the grinding wheel 14. Since the indicated density profile 40 shows that the inspected grinding wheel 14 is of relatively uniform density, the grinding wheel 14 is a good grinding wheel and is likely to perform well in grinding operations involving work rolls. The work rolls ground with the grinding wheel 14 illustrated in FIG. 9 are likely not to be imprinted with patterning and perform well in rolling operations on metal sheet, particularly aluminum sheet.

While the present invention was described with reference to preferred embodiments, those skilled in the art may make modifications and alterations to the present invention without departing from the scope and spirit of the invention. Accordingly, the foregoing detailed description is intended to be illustrative rather than restrictive. The present invention is defined by the appended claims, and all changes to the invention that fall within the meaning and range of equivalency of the claims are to be embraced within their scope

The invention claimed is:

1. A method of characterizing grinding wheels comprising: transmitting sound waves through a grinding wheel configured for the production of metal sheet material;
    recording amplitude attenuation of the sound waves passing through the grinding wheel; and
    analyzing variations in the amplitude attenuation to determine uniformity of density of the grinding wheel, wherein determining the uniformity of density of the grinding wheel comprises calculating an average deviation of a mean of the grinding wheel density based solely on the variations in the amplitude attenuation.

2. The method of claim 1, further comprising transmitting the sound waves from an ultrasonic transmitting apparatus to an ultrasonic receiving apparatus.

3. The method of claim 1, wherein analyzing the amplitude attenuation further comprises a computer configured to store the differences in density as an indicated density profile in a computer memory.

4. The method of claim 1, further comprising displaying the average deviation from the mean on a computer screen for visual inspection.

5. The method of claim 4, further comprising displaying at least a two dimensional image of the average deviation from the mean on the computer screen.

6. The method of claim 1, further comprising comparing the average deviation from the mean of the grinding wheel with the average deviation from the mean of grinding wheels of known operational quality.

7. The method of claim 1 further comprising transmitting sound waves in the range of about 100 KHz to 2 MHz through the grinding wheel.

8. The method of claim 1 comprising transmitting the sound waves to the grinding wheel using ambient air as the sound conducting medium.

9. The method of claim 1, wherein the transmitting of the sound waves through the grinding wheel comprises:
   supporting the grinding wheel on a test stand;
   positioning an ultrasonic transmitting and receiving apparatus proximate to opposite sides of the grinding wheel;
   moving the ultrasonic transmitting and receiving apparatus about the grinding wheel; and
   transmitting the sound waves through the grinding wheel.

10. The method of claim 1, wherein the transmitting of sound waves through the grinding wheel comprises:
    rotatably supporting the grinding wheel on a test stand;
    positioning the ultrasonic transmitting and receiving apparatus proximate to the opposite sides of the grinding wheel;
    rotating the grinding wheel on the test stand; and
    transmitting the sound waves through the grinding wheel.

11. A method of characterizing grinding wheels comprising:
    transmitting sound waves through a grinding wheel configured for the production of metal sheet material;
    recording amplitude attenuation of the sound waves passing through the grinding wheel; and
    calculating an average deviation from a mean of the amplitude attenuation of the sound waves passing through the grinding wheel, based solely on variations in the amplitude attenuation of the sound waves, to evaluate the density profile of the grinding wheel.

12. The method of claim 11, further comprising transmitting the sound waves from an ultrasonic transmitting apparatus to an ultrasonic receiving apparatus.

13. The method of claim 11, further comprising displaying the density profile on a computer screen for visual inspection.

14. The method of claim 11, further comprising displaying at least a two dimensional image of the average deviation from the mean on the computer screen.

15. The method of claim 14, further comprising comparing the average deviation from the mean of the grinding wheel with the average deviation from the mean of grinding wheels of known operational quality.

16. The method of claim 11 comprising transmitting the sound waves to the grinding wheel using ambient air as the sound conducting medium.

17. The method of claim 11, wherein the transmitting of the sound waves through the grinding wheel comprises:
    supporting the grinding wheel on a test stand;
    positioning an ultrasonic transmitting and receiving apparatus proximate to opposite sides of the grinding wheel;
    moving the ultrasonic transmitting and receiving apparatus about the grinding wheel; and
    transmitting the sound waves through the grinding wheel.

18. The method of claim 11, wherein the transmitting of sound waves through the grinding wheel comprises:
    rotatably supporting the grinding wheel on a test stand;
    positioning the ultrasonic transmitting and receiving apparatus proximate to the opposite sides of the grinding wheel;
    rotating the grinding wheel on the test stand; and
    transmitting the sound waves through the grinding wheel.

* * * * *